United States Patent [19]

Hershel et al.

[11] Patent Number: 4,783,144

[45] Date of Patent: Nov. 8, 1988

[54] THIN OPTICAL MEMBRANES AND METHOD OF MAKING THE SAME

[75] Inventors: Ronald S. Hershel, Albany, Oreg.; Ray Winn, North Hollywood, Calif.

[73] Assignee: Advanced Semiconductor Products, Inc., Compton, Calif.

[21] Appl. No.: 842,168

[22] Filed: Mar. 20, 1986

Related U.S. Application Data

[60] Continuation-in-part of Ser. No. 594,474, Mar. 28, 1984, abandoned, which is a division of Ser. No. 326,488, Dec. 2, 1981, Pat. No. 4,453,828.

[51] Int. Cl.$^4$ .............................. G02B 5/00; B05D 5/00
[52] U.S. Cl. ..................................... 350/320; 350/321; 427/162
[58] Field of Search ................ 350/1.1, 320, 171, 582, 350/321; 156/74, 246; 427/162

[56] References Cited

U.S. PATENT DOCUMENTS

| 3,438,694 | 4/1969 | Reid et al. | 350/171 |
|---|---|---|---|
| 4,378,953 | 4/1983 | Winn | 264/311 |
| 4,536,240 | 8/1985 | Winn | 264/311 |

Primary Examiner—Bruce Y. Arnold
Attorney, Agent, or Firm—Nilsson, Robbins, Dalgarn, Berliner, Carson & Wurst

[57] ABSTRACT

Optical membranes having embossed data on their surfaces are made by dispensing the polymer/solvent mixture onto a rotatable supporting surface bearing the embossed data, spinning the rotatable surface under conditions sufficient to form the membrane from the polymer and removing the membrane, after formation, from the rotatable surface. Such membranes can be light-transmissive, light-reflective or, as desired, partially reflective and partially transmissive.

9 Claims, No Drawings

THIN OPTICAL MEMBRANES AND METHOD OF MAKING THE SAME

This is a continuation-in-part of application Ser. No. 594,474, filed Mar. 28, 1984, now abandoned, which application is a division of U.S. patent application Ser. No. 326,488, filed Dec. 2, 1981, now U.S. Pat. No. 4,453,828.

This invention relates to methods for making thin optical membranes and the product resulting therefrom. This application is a continuation-in-part of U.S. patent application Ser. No. 594,474, filed Mar. 28, 1984, entitled, "Apparatus and Methods for Measuring the Optical Thickness and Index of Refraction of Thin, Optical Membranes," (now abandoned) which application is a division of U.S. patent application Ser. No. 326,488, filed Dec. 2, 1981, entitled, "Apparatus and Methods for Measuring the Optical Thickness and Index of Refraction of Thin, Optical Membranes," now U.S. Pat. No. 4,453,828. By this reference, we incorporate the entire disclosures of these applications in this application. See also U.S. Pat. No. 4,536,240, issued Aug. 20, 1985, and entitled, "Method of Forming Thin Optical Membranes"; this patent issued from U.S. patent application Ser. No. 468,468, filed Feb. 22, 1983, as a division of U.S. patent application Ser. No. 326,489 now U.S. Pat. No. 4,378,953.

The thin, optical membranes disclosed and claimed in U.S. patent application Ser. Nos. 594,474 and 326,488, and referred to above, have new uses not disclosed there. These membranes exhibit excellent elasticity and homogeneity. In particular, these membranes can be used to copy and reproduce large quantities of data in compressed form and with substantially no distortion, especially where these membranes are mounted on mechanically, thermally stable frames or other supports. To effect this copying, we simply form the thin, optical membranes on a surface which carries a large quantity of data in highly compressed form. Our membranes form an accurate, precise duplicate of the data from the original, and can then be utilized as an original for replication and for storage of the data.

In one embodiment, we form a thin, optical membrane on a surface carrying large quantities of data in compressed form as an embossment on the surface. By forming the thin, optical membrane on such embossed surfaces, we replicate identically the surface embossment and the data contained in that embossment. Such membranes are capable of being supported at their peripheries and are capable of being removed, substantially intact, from the surfaces on which they are formed. These membranes can have a capacity to transmit light incident on them, to reflect light incident on them, or to reflect some of the incident light and to transmit some of the incident light, both in substantial amounts.

The thin, optical membranes of this invention can be made by dispensing a polymer/solvent mixture onto a rotatable supporting surface bearing embossed data, spinning the rotatable surface under condition sufficient to form the membranes from the polymer, and removing the membrane, after formation, from the rotatable surface. Made in this way, the thin optical membranes have the data from the rotatable surface embossed on their surfaces.

The thin, optical membranes of this invention can have the capacity to transmit or reflect incident light energy with wavelengths in the ultraviolet range, in the visible range, and in the infrared range. These membranes can also have the capacity to transmit a major or minor amount of incident light over part of their surface area, and to reflect a major or minor amount of light over the remainder of their surface area.

In one embodiment, our data-carrying, thin, optical membranes can have a nominal thickness in the range of about 0.5 to about 10 micrometers, and exhibit edge-to-edge variations in nominal thickness of less than about 2%. In any one membrane, variations in nominal thickness from edge to edge of the membrane can be limited to less than about 2%, and preferably less than about 1%. Unit-to-unit variations in nominal thickness of these membranes can be limited to less than about 2%.

In one embodiment, these membranes can be highly light-transmissive. Specifically, such light-transmissive membranes transmit in the range of about 84% to about 99% of incident light and can be made to transmit at least about 96%, 98% or even 99% of incident light at one or more wavelengths of light in the range of about 260 to about 1,000 nanometers.

What is claimed is:

1. A thin, optical membrane capable of being supported at its periphery, and capable of being removed, substantially intact, from the surface on which said membrane is formed, and having a predetermined thickness of at least about 0.5 micrometers, said membrane having a capacity to transmit at least some light incident thereon, said membrane being made by dispensing a polymer/solvent mixture onto a rotatable supporting surface bearing embossed data, spinning said rotatable surface under conditions sufficient to form said membrane from said polymer, and removing said membrane, after formation, from said rotatable surface, said membrane having said embossed data on its surface.

2. A thin, optical membrane capable of being removed, substantially intact, from the surface on which said membrane is formed, and having a predetermined thickness of at least about 0.5 micrometers, said membrane having a capacity to transmit at least some of the light incident thereon, said membrane being made by dispensing a polymer/solvent mixture onto a rotatable supporting surface bearing embossed data, spinning said rotatable surface under conditions sufficient to form said membrane from said polymer, and removing said membrane, after formation, from said rotatable surface, said membrane having said data embossed on its surface.

3. A thin, optical membrane having a thickness of at least about 0.5 micrometers, said optical membrane being capable of being supported at its periphery, and being capable of being removed, substantially intact, from the surface on which said membrane is formed, said membrane having a capacity to transmit at least some of the light incident thereon, said membrane having data embossed on its surface, said membrane being made by a spinning process from a polymer/solvent mixture on a surface bearing said embossed data.

4. A thin, optical membrane capable of being removed, substantially intact, from the surface on which said membrane is formed, and having a predetermined thickness of at least about 0.5 micrometers, said membrane carrying data in embossed form on its surface, said membrane being made by dispensing a polymer/solvent mixture onto a rotatable supporting surface carrying said data in embossed form, spinning said rotatable surface under conditions sufficient to form said membrane from said polymer, and removing said membrane, after formation, from said rotatable surface.

5. A thin, optical membrane capable of being supported at its periphery, capable of being removed, substantially intact, from the surface on which said membrane is formed, and having a predetermined thickness of at least about 0.5 micrometers, said membrane having data embossed on its surface, said membrane being made by dispensing a polymer/solvent mixture onto a rotatable supporting surface carrying said embossed data, spinning said rotatable surface under conditions sufficient to form said membrane from said polymer, and removing said membrane, after formation, from said rotatable surface.

6. A thin, optical membrane capable of being removed, substantially intact, from the surface on which said membrane is formed, and having a thickness of at least about 0.5 micrometers, said membrane being made by dispensing a polymer/solvent mixture onto a rotatable supporting surface bearing embossed data, spinning said rotatable surface under conditions sufficient to form said membrane from said polymer, and removing said membrane, after formation, from said rotatable surface, said membrane having said data embossed on its surface.

7. A method for making a thin, optical membrane carrying embossed data thereon comprising dispensing a polymer/solvent mixture onto a rotatable supporting surface bearing said embossed data, spinning the rotatable surface under conditions sufficient to form said membrane from said polymer, and removing said membrane, after formation, from said rotatable surface, said membrane having said embossed data on its surface, said membrane being capable of being supported at its periphery, and capable of being removed, substantially intact, from the surface on which the membrane was formed, and said membrane having a predetermined thickness of at least about 0.5 micrometer.

8. A method for making a thin, optical membrane carrying embossed data thereon comprising dispensing a polymer/solvent mixture onto a rotatable supporting surface bearing said embossed data, spinning the rotatable surface under conditions sufficient to form said membrane from said polymer, and removing said membrane, substantially intact, after formation, from said rotatable surface, said membrane having said data embossed on its surface, said membrane having a predetermined thickness of at least about 0.5 micrometer, and a capacity to transmit at least some light incident thereon.

9. A method for making a thin, optical membrane carrying embossed data thereon comprising dispensing a polymer/solvent mixture onto a rotatable supporting surface carrying said data in embossed form, spinning the rotatable surface under conditions sufficient to form said membrane from said polymer, and removing said membrane, substantially intact, after formation, from said rotatable surface, said membrane carrying said data in embossed form on its surface, said membrane having the capacity to reflect at least some light incident thereon.

* * * * *